(12) United States Patent
Kim et al.

(10) Patent No.: US 9,257,613 B2
(45) Date of Patent: Feb. 9, 2016

(54) SEMICONDUCTOR LIGHT EMITTING DEVICE

(71) Applicant: LG INNOTEK CO., LTD., Seoul (KR)

(72) Inventors: Geun Ho Kim, Seoul (KR); Sung Kyoon Kim, Seoul (KR); Hee Seok Choi, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 107 days.

(21) Appl. No.: 13/759,291

(22) Filed: Feb. 5, 2013

(65) Prior Publication Data

US 2013/0146922 A1    Jun. 13, 2013

Related U.S. Application Data

(63) Continuation of application No. 12/997,431, filed as application No. PCT/KR2009/003196 on Jun. 15, 2009, now Pat. No. 8,373,193.

(30) Foreign Application Priority Data

Jun. 16, 2008   (KR) .................. 10-2008-0056210

(51) Int. Cl.
*H01L 33/00* (2010.01)
*H01L 33/46* (2010.01)
*A01H 5/02* (2006.01)

(52) U.S. Cl.
CPC ........ *H01L 33/46* (2013.01); *A01H 5/02* (2013.01); *H01L 2224/48091* (2013.01); *H01L 2224/49107* (2013.01); *H01L 2224/73265* (2013.01)

(58) Field of Classification Search
CPC .................................................... H01L 33/00
See application file for complete search history.

(56) References Cited

U.S. PATENT DOCUMENTS

| | | | |
|---|---|---|---|
| 6,268,618 B1 | 7/2001 | Miki et al. .................. 257/99 |
| 6,586,043 B1 | 7/2003 | Sinha | |
| 6,936,859 B1 | 8/2005 | Uemura et al. | |
| 2003/0129310 A1 | 7/2003 | Sinha | |
| 2004/0222434 A1* | 11/2004 | Uemura et al. ............ 257/99 |
| 2006/0081869 A1 | 4/2006 | Lu et al. | |
| 2009/0184329 A1 | 7/2009 | Miki et al. | |
| 2009/0250716 A1 | 10/2009 | Haberern et al. | |
| 2010/0295079 A1* | 11/2010 | Melman ..................... 257/98 |
| 2011/0018022 A1 | 1/2011 | Okabe et al. | |

FOREIGN PATENT DOCUMENTS

| | | |
|---|---|---|
| CN | 1993837 A | 7/2007 |
| EP | 0 622 858 A2 | 11/1994 |
| JP | 2008-041866 A | 2/2008 |

(Continued)

OTHER PUBLICATIONS

European Examination Report dated Aug. 12, 2014 issued in Application No. 09 766 808.1.
Antonets, I.V., et al., "Conducting and Reflecting Properties of Thin Metal Films," Technical Physics, (Nov. 1, 2004), 49:11:1496-1500.
Derwent abstract 2008 "Light source packaging structure."
International Search Report dated Feb. 17, 2010.
European Search Report dated Jul. 6, 2011.

(Continued)

*Primary Examiner* — Marvin Payen
(74) *Attorney, Agent, or Firm* — Ked & Associates, LLP

(57) ABSTRACT

Disclosed is a semiconductor light emitting device. The light emitting device includes a first conductive type semiconductor layer; an active layer on the first conductive type semiconductor layer; and a first electrode pad including a plurality of reflective layers on the first conductive type semiconductor layer.

22 Claims, 2 Drawing Sheets

(56) References Cited

FOREIGN PATENT DOCUMENTS

| | | |
|---|---|---|
| JP | 2004-349301 A | 12/2009 |
| KR | 10-0675208 B1 | 1/2007 |
| KR | 10-2007-0041506 A | 4/2007 |
| KR | 10-2009-0015633 A | 2/2009 |

OTHER PUBLICATIONS

United States Office Action dated Apr. 3, 2012 issued in U.S. Appl. No. 12/997,431.
European Search Report dated Feb. 20, 2012.
European Office Action dated Nov. 9, 2012.
Chinese Office Action dated Nov. 14, 2012.

\* cited by examiner

SEMICONDUCTOR LIGHT EMITTING DEVICE

CROSS-REFERENCE TO RELATED APPLICATIONS

This application is a Continuation Application of prior U.S. patent application Ser. No. 12/997,431 filed Dec. 10, 2010 (now U.S. Pat. No. 8,373,193 issued Feb. 12, 2013), which is a National Stage application under 35 U.S.C. §365 of International Application No. PCT/KR2009/003196 filed on Jun. 15, 2009, which claims priority under 35 U.S.C. §119 to Korean Application No. 10-2008-0056210 filed on Jun. 16, 2008 which claims priority to, whose entire disclosures are hereby incorporated by reference.

BACKGROUND

1. Field

The embodiment relates to a semiconductor light emitting device.

2. Background

Groups III-V nitride semiconductors have been extensively used as main materials for light emitting devices, such as a light emitting diode (LED) or a laser diode (LD), due to the physical and chemical characteristics thereof. In general, the groups III-V nitride semiconductors include a semiconductor material having a composition formula of $In_xAl_yGa_{1-x-y}N$ ($0 \leq x \leq 1$, $0 \leq y \leq 1$, and $0 \leq x+y \leq 1$).

The LED is a semiconductor device, which transmits/receives signals by converting an electric signal into infrared ray or light using the characteristics of compound semiconductors. The LED is also used as a light source.

The LED or LD using the nitride semiconductor material is mainly used for the light emitting device to provide the light. For instance, the LED or the LD is used as a light source for various products, such as a keypad light emitting part of a cellular phone, an electric signboard, and a lighting device.

The above references are incorporated by reference herein where appropriate for appropriate teachings of additional or alternative details, features and/or technical background.

DISCLOSURE

Technical Problem

The embodiment provides a semiconductor light emitting device including a plurality of reflective layers formed on a first electrode pad and/or a second electrode pad.

The embodiment provides a semiconductor light emitting device including an electrode pad having an adhesive layer, a first reflective layer, a barrier metal layer and a second reflective layer sequentially stacked on a semiconductor layer.

Technical Solution

An embodiment provides a semiconductor light emitting device, comprising a first conductive type semiconductor layer; an active layer on the first conductive type semiconductor layer; and a first electrode pad including a plurality of reflective layers on or under the first conductive type semiconductor layer.

An embodiment provides a semiconductor light emitting device, comprising a light emitting structure including a first conductive type semiconductor layer and a second conductive type semiconductor layer; a first electrode pad including a plurality of reflective layers on one side of the first conductive type semiconductor layer; a second electrode pad including a plurality of reflective layers on one side of the second conductive type semiconductor layer; and a second electrode layer on an another side of the second conductive type semiconductor layer.

Advantageous Effects

The embodiment can improve the external quantum efficiency.

The embodiment can improve the quantity of reflective light in a semiconductor light emitting device.

The embodiment can improve the light efficiency of a light emitting diode package.

BRIEF DESCRIPTION OF THE DRAWINGS

The embodiments will be described in detail with reference to the following drawings in which like reference numerals refer to like elements wherein.

DETAILED DESCRIPTION

[Best Mode]

[Mode for Invention]

Hereinafter, a semiconductor light emitting device according to the embodiment will be described in detail with reference to accompanying drawings. In the description of the embodiments, it will be understood that, when a layer is referred to as being "on" or "under" another layer, it can be "directly" or "indirectly" on another layer or one or more intervening layers may also be present. Such a position of the layer has been described with reference to the drawings. In the description about the embodiment, the thickness of elements shown in the accompanying drawings are for an illustrative purpose only, and the embodiment is not limited thereto.

Figure 1:
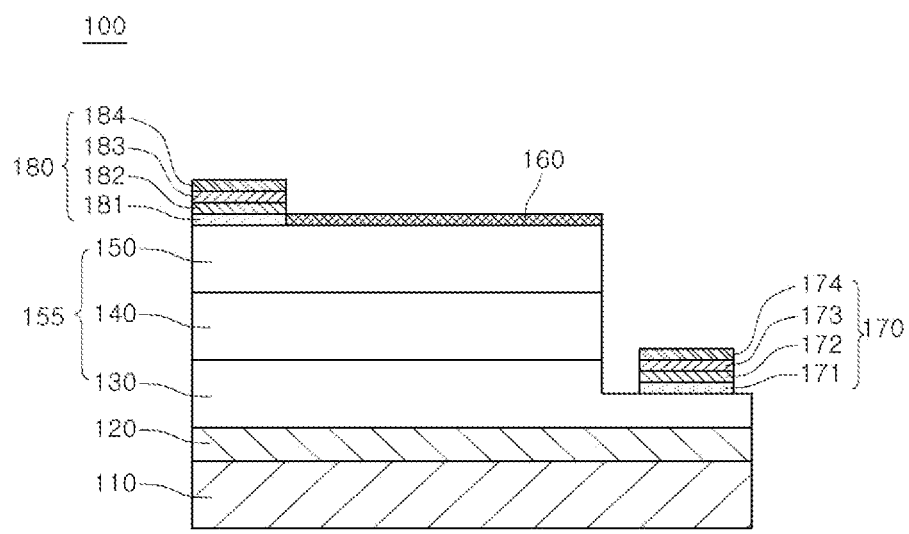
FIG. 1 is a side sectional view showing a semiconductor light emitting device according to the first embodiment.
Figure 2:
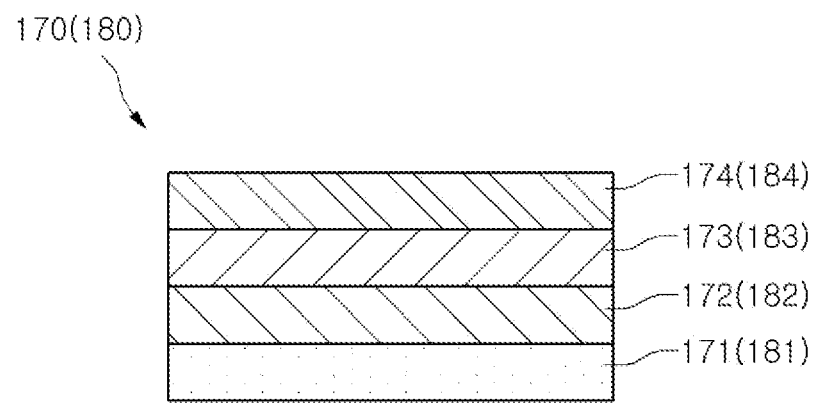
FIG. 2 is a sectional view showing the detailed structure of first and second electrode pads of FIG. 1.

FIG. 1 is a side sectional view showing a semiconductor light emitting device according to the first embodiment, and FIG. 2 is a sectional view showing the detailed structure of first and second electrode pads of FIG. 1.

Referring to FIG. 1, the semiconductor light emitting device 100 includes a substrate 110, a buffer layer 120, a first conductive type semiconductor layer 130, an active layer 140, a second conductive type semiconductor layer 150, a second electrode layer 160, a first electrode pad 170, and a second electrode pad 180.

The substrate 110 may include one selected from the group consisting of Al2O3, GaN, SiC, ZnO, Si, GaP, InP, GaAs and conductive substrates. A concave-convex pattern can be formed on the substrate 110, but the embodiment is not limited thereto.

A nitride semiconductor can be grown on the substrate 110. In this case, growth equipment may be selected from the group consisting of E-beam evaporator, PVD (physical vapor deposition), CVD (chemical vapor deposition), PLD (plasma laser deposition), dual-type thermal evaporator, sputtering, and MOCVD (metal organic chemical vapor deposition), but the embodiment is not limited thereto.

The buffer layer 120 can be formed on the substrate 110. The buffer layer 120 may include a material capable of reducing the mismatch of the lattice constant between the buffer layer 120 and the substrate 110. For instance, the buffer layer 120 may include a single crystalline material or a group III-V compound semiconductor material, such as GaN, AlN, AlGaN, InGaN, Inn, InAlGaN, and AlInN. The buffer layer 120 can be omitted.

An undoped semiconductor layer (not shown) can be formed on the buffer layer 120 or the substrate 110. The undoped semiconductor layer may include an undoped GaN layer.

The first conductive type semiconductor layer 130 is formed on the buffer layer 120. The first conductive type semiconductor layer 130 can be prepared as a single layer or a multiple layer by using a group III-V compound semiconductor material doped with a first conductive dopant, such as GaN, AlN, AlGaN, InGaN, Inn, InAlGaN, and AlInN.

If the first conductive type semiconductor layer 130 is an N type semiconductor layer, the first conductive dopant includes an N type dopant, such as Si, Ge, Sn, Se, or Te. The first conductive type semiconductor layer 130 may serve as an electrode contact layer, but the embodiment is not limited thereto.

The active layer 140 is formed on the first conductive type semiconductor layer 130. The active layer 140 can be prepared as a single quantum well structure or a multiple quantum well structure.

The active layer 140 may have a stack structure including a well layer and a barrier layer, which are made from compound semiconductors of group III-V elements. For example, the active layer 140 may have a stack structure of an InGaN well layer/GaN barrier layer, or AlGaN well layer/GaN barrier layer. In addition, the active layer 140 may include a material having bandgap energy according to the wavelength of light emitted from the active layer 140.

A conductive clad layer may be formed on and/or under the active layer 140. The conductive clad layer may include an AlGaN-based semiconductor.

The second conductive type semiconductor layer 150 is formed on the active layer 140. The second conductive type semiconductor layer 150 includes the compound semiconductors of group III-V elements doped with the second conductive dopant. For instance, the second conductive layer 150 can be prepared as a single layer or a multiple layer by using one selected from the group consisting of GaN, AlN, AlGaN, InGaN, InN, InAlGaN, and AlInN. If the second conductive type semiconductor layer 150 is a P type semiconductor layer, the second conductive dopant includes the P type dopant such as Mg or Ze. The second conductive type semiconductor layer 150 may serve as an electrode contact layer, but the embodiment is not limited thereto.

The first conductive type semiconductor layer 130, the active layer 140 and the second conductive type semiconductor layer 150 may constitute a light emitting structure 155. In addition, the first conductive type semiconductor layer 130 may include a P type semiconductor layer and the second conductive type semiconductor layer 150 may include an N type semiconductor layer. Further, a third conductive type semiconductor layer, such as an N type semiconductor layer or a P type semiconductor layer, can be formed on the second conductive type semiconductor layer 150. Accordingly, the light emitting structure 155 may include at least one of an N-P junction structure, a P-N junction structure, an N-P-N junction structure, and a P-N-P junction structure.

The second electrode layer 160 is formed on the second conductive type semiconductor layer 150. The second electrode layer 160 may include a transparent electrode layer or a reflective electrode layer. The transparent electrode layer may include one selected from the group consisting of ITO (indium tin oxide), IZO (indium zinc oxide), IZTO (indium zinc tin oxide), IAZO (indium aluminum zinc oxide), IGZO (indium gallium zinc oxide), IGTO (indium gallium tin oxide), AZO (aluminum zinc oxide), ATO (antimony tin oxide), RuOx, TiOx, and IrOx. In addition, the reflective electrode layer may include one selected from the group consisting of Al, Ag, Pd, Rh, Pt, and Ir.

The second electrode layer 160 can uniformly diffuse input current or the second electrode layer 160 can reflect or refract the emitted light.

The first electrode pad 170 is formed at one side of the first conductive type semiconductor layer 130 and the second electrode pad 180 is formed at one side of the second conductive type semiconductor layer 150. If the third conductive type semiconductor layer (not shown) is formed on the second conductive type semiconductor layer 150, the second electrode pad 180 is formed on the third conductive type semiconductor layer.

One side of the first conductive type semiconductor layer 130 may be exposed through a mesa etching process. The mesa etching process can be performed after the second conductive type semiconductor layer 150 or the second electrode layer 160 has been formed.

The second electrode pad 180 can directly make contact with the second electrode layer 160 and/or the second conductive type semiconductor layer 150. The second electrode pad 180 is formed on one side of a top surface of the second conductive type semiconductor layer 150, and the second electrode layer 160 makes contact with an outer peripheral portion of the second electrode pad 180. In addition, the second electrode pad 180 can be formed on the second electrode layer 160 while indirectly making contact with the second conductive type semiconductor layer 150. Further, the second electrode pad 180 can directly make contact with the second conductive type semiconductor layer 150 through an opening (not shown) of the second electrode layer 160.

The first electrode pad 170 includes a plurality of reflective layers 172 and 174, and the second electrode pad 180 includes a plurality of reflective layers 182 and 184. The first and second electrode pads 170 and 180 may have the same structure and one of the first and second electrode pads 170 and 180 can be prepared as a normal pad without the reflective layers. According to the embodiment, the number of the first and second electrode pads 170 and 180 may vary depending on the size of the device, and the embodiment is not limited thereto.

Referring to FIGS. 1 and 2, the first electrode pad 170 includes a first adhesive layer 171, a first reflective layer 172, a first barrier metal layer 173, and a second reflective layer 174.

The first adhesive layer 171 is formed on the first conductive type semiconductor layer 130. The first adhesive layer 171 may include a material having superior adhesive property with respect to the first conductive type semiconductor layer 130. For instance, the first adhesive layer 171 includes at least one selected from the group consisting of Cr, V, W, Ti, an APC (Ag+Pd+Cu) alloy, a Cr-first metal alloy, and a Ti-second metal alloy. The first metal includes at least one of Fe, Tu, Mo, Al and Ag, and the second metal includes at least one of Fe, Tu, Mo, Al and Ag.

If the first adhesive layer 171 has a thick thickness, the light is absorbed in the first adhesive layer 171. Thus, the first adhesive layer 171 may have a thickness sufficient for transmitting the light. For instance, the first adhesive layer 171 has a thickness of about 1 to 60,000 Å.

The first reflective layer 172 is formed on the first adhesive layer 171 and includes a material having superior reflectance. For instance, the first reflective layer 172 may include at least one selected from the group consisting of Al, Ag, an APC (Ag+Pd+Cu) alloy, an Al-third metal alloy, and an Ag-fourth metal alloy. The third metal includes at least one of Cr, Fe, Mo and Tu. In addition, the fourth metal includes at least one of Cr, Fe, Mo and Tu. The first reflective layer 172 may have a thickness of about 1 to 50,000 Å.

The first barrier metal layer 173 is formed on the first reflective layer 172 and the second reflective layer 174 is formed on the first barrier metal layer 173. The first barrier metal layer 173 is a boundary layer between the first and second reflective layers 172 and 174 and allows the first and second reflective layers 172 and 174 to effectively reflect the light. In addition, the first barrier metal layer 173 prevents the first and second reflective layers 172 and 174 from reacting with each other. The first barrier metal layer 173 can be formed by using various metals. For instance, the first barrier metal layer 173 can be prepared as a single layer or a multiple layer by using Ni or Ni—N.

The second reflective layer 174 may include at least one selected from the group consisting of Al, Ag, an APC (Ag+Pd+Cu) alloy, an Al-fifth metal alloy, and an Ag-sixth metal alloy. The fifth metal includes at least one of Cr, Fe, Mo and Tu. In addition, the sixth metal includes at least one of Cr, Fe, Mo and Tu. The second reflective layer 174 may have a thickness of about 1 to 50,000 Å.

The second reflective layer 174 may include a material identical to or different from that of the first reflective layer 172.

The second electrode pad 180 includes a second adhesive layer 181, a third reflective layer 182, a second barrier metal layer 183 and a fourth reflective layer 184. The second electrode pad 180 has the structure the same as that of the first electrode pad 170, so the structure of the second electrode pad 180 will be briefly described with reference to the layers 171 to 174 of the first electrode pad 170.

The second adhesive layer 181 is formed on the second conductive type semiconductor layer 150 or the second electrode layer 160. The second adhesive layer 181 directly makes contact with the second conductive type semiconductor layer 150 and/or the second electrode layer 160.

The second adhesive layer 181 may include a material having superior adhesive property with respect to the second conductive type semiconductor layer 150. For instance, the second adhesive layer 181 includes at least one selected from the group consisting of Cr, V, W, Ti, an APC (Ag+Pd+Cu) alloy, a Cr-first metal alloy, and a Ti-second metal alloy. The first metal includes at least one of Fe, Tu, Mo, Al and Ag, and the second metal includes at least one of Fe, Tu, Mo, Al and Ag. The second adhesive layer 181 and the first adhesive layer 171 can be simultaneously formed by using the same material.

If the second adhesive layer 181 has a thick thickness, the light is absorbed in the second adhesive layer 181. Thus, the second adhesive layer 181 may have a thickness sufficient for transmitting the light. For instance, the second adhesive layer 181 has a thickness of about 1 to 60,000 Å.

The third reflective layer 182 is formed on the second adhesive layer 181. The third reflective layer 182 and the first reflective layer 172 can be simultaneously formed by using the same material.

The third reflective layer 182 includes a material having superior reflectance. For instance, the third reflective layer 182 may include at least one selected from the group consisting of Al, Ag, an APC (Ag+Pd+Cu) alloy, an Al-third metal alloy, and an Ag-fourth metal alloy. The third metal includes at least one of Cr, Fe, Mo and Tu. In addition, the fourth metal includes at least one of Cr, Fe, Mo and Tu. The third reflective layer 182 may have a thickness of about 1 to 50,000 Å.

The second barrier metal layer 183 is formed on the third reflective layer 182 and the fourth reflective layer 184 is formed on the second barrier metal layer 183.

The second barrier metal layer 183 prevents the third and fourth reflective layers 182 and 184 from reacting with each other. For instance, the second barrier metal layer 183 can be prepared as a single layer or a multiple layer by using Ni or Ni—N. The second barrier metal layer 183 and the first barrier metal layer 173 can be simultaneously formed by using the same material.

The fourth reflective layer 184 may include at least one selected from the group consisting of Al, Ag, an APC (Ag+Pd+Cu) alloy, an Al-fifth metal alloy, and an Ag-sixth metal alloy. The fifth metal includes at least one of Cr, Fe, Mo and Tu. In addition, the sixth metal includes at least one of Cr, Fe, Mo and Tu. The fourth reflective layer 184 may have a thickness of about 1 to 50,000 Å. The fourth reflective layer 184 and the second reflective layer 174 can be simultaneously formed by using the same material.

The fourth reflective layer 184 may include the material identical to or different from that of the third reflective layer 183.

The first and second electrode pads 170 and 180 can be formed as follows. A photoresist layer is coated on the top surface of the semiconductor layer and a pad region is exposed through a lithography process. Then, the layers 171 to 174 of the first electrode pad 170 and the layers 181 to 184 of the second electrode pad 180 are sequentially formed. The layers 171 to 174 of the first electrode pad 170 and the layers 181 to 184 of the second electrode pad 180 are deposited in the vacuum evaporator through the E-beam evaporation scheme. After that, layers, which are unnecessarily formed on the photoresist layer, are removed. Such a method for forming the first and second electrode pads 170 and 180 can be changed, and the embodiment is not limited thereto.

In the semiconductor light emitting device 100, if current is applied to the first and second electrode pads 170 and 180, light generated from the active layer 140 is omni-directionally emitted. Some light is travelled toward the first or second electrode pad 170 or 180, and then reflected from the first and third reflective layers 172 and 182. In addition, light travelled from the outside to the inside of the device is reflected from the second or fourth reflective layer 174 or 184. Thus, the light efficiency can be improved.

The semiconductor light emitting device 100 is a lateral type semiconductor light emitting device. According to another embodiment, a vertical type semiconductor light emitting device can be used for the semiconductor light emitting device 100.

The vertical type semiconductor light emitting device may include a reflective electrode layer serving as the second electrode pad and a conductive support member formed on the second conductive type semiconductor layer and the growth substrate under the first conductive type semiconductor is removed. The reflective electrode layer is the second electrode pad where the adhesive layer, the third reflective layer, the second barrier metal layer and the fourth reflective layer are sequentially formed, but the embodiment is not limited thereto.

After the growth substrate under the first conductive type semiconductor layer has been removed, the conductive support member is placed on the base and the wet etching and/or the dry etching process is performed to expose the first conductive type semiconductor layer. As the first conductive type semiconductor layer is exposed, the first electrode pad is formed on the first conductive type semiconductor layer. The first electrode pad includes the first adhesive layer, the first reflective layer, the first barrier metal layer and the second metal layer. The stack structure and material for the first electrode pad is similar to those of the first embodiment. The electrode pad can be properly selected within the scope of the present invention.

Figure 3:
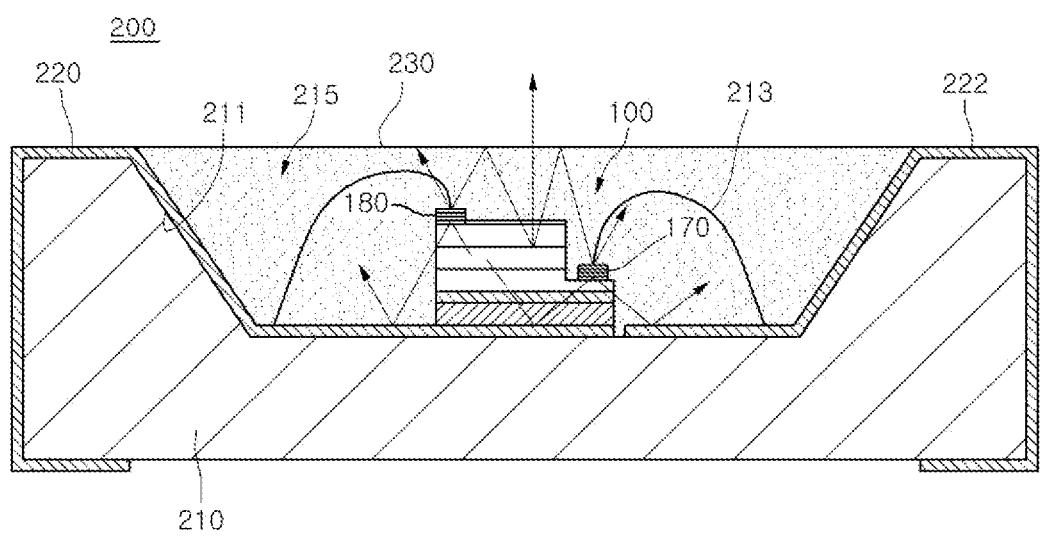
FIG. 3 is a side sectional view showing a light emitting device package using the semiconductor light emitting device of FIG. 1.

FIG. 3 is a side sectional view showing a light emitting device package using the semiconductor light emitting device of FIG. 1.

Referring to FIG. 3, the light emitting device package 200 includes a package body 210 having a cavity 215, a plurality of electrode leads 220 and 222, a semiconductor light emitting device 100, a wire 213 and a resin material 230.

The package body 210 may include one selected from the group consisting of PPA (polyphthalamide), liquid crystal polymer, resin material (for example, SPS (syndiotactic polystyrene)), an MCPCB (metal core PCB), a PCB, a ceramic PCB, FR-4, AlN (aluminum nitride), and SiC (silicon carbide). In addition, the package body 210 can be prepared in the form of a COB (chip on board) or a multiple substrate structure. The embodiment may not limit the material, the structure and the shape of the package body 210.

The cavity 215 is formed at an upper portion of the cavity body 210. The cavity 215 may be omitted.

A periphery wall 211 of the cavity 215 is inclined or perpendicular to the bottom of the cavity 215. The first and second electrode leads 222 and 220 are disposed in the cavity 215. The first and second electrode leads 222 and 220 may include metals having superior reflective property.

Other ends of the first and second electrode leads 222 and 220 are exposed out of the cavity body 210 to serve as external electrodes.

The semiconductor light emitting device 100 is die-bonded onto the first electrode lead 222 by an adhesive (not show) and electrically connected to the first and second electrode pads 170 and 180 through the wire 213.

The cavity 215 is filled with the resin material 230, such as epoxy or silicon resin. Phosphor may be added to the resin material 230. The top surface of the resin material 230 has a flat shape, a convex lens shape or a concave shape. A lens (not shown) can be formed on the resin material 230 through injection molding or attached onto the resin material 230.

Referring to FIGS. 1 and 3, in the light emitting device package 200, if current is applied to the first and second electrode leads 222 and 220, light generated from the semiconductor light emitting device 100 is omni-directionally emitted. The light is reflected from the first and second reflective layers 172 and 174 of the first electrode pad 170 and the third and fourth reflective layers 182 and 184 of the second electrode pad 180, respectively. Thus, the light efficiency of the light emitting device package 200 can be improved and the reliability of the light emitting device package 200 can be can be enhanced.

The second electrode layer (160 of FIG. 1) of the semiconductor light emitting device 100 may be a transparent electrode.

Meanwhile, when the semiconductor light emitting device 100 is mounted on the electrode leads 220 and 222 through the flip scheme, the second electrode layer (160 of FIG. 1) may serve as the reflective electrode layer to reflect the incident light.

At least one lateral type or vertical type light emitting device can be installed in the light emitting device package 200 in the form of a chip, but the embodiment is not limited thereto. In addition, the light emitting device package 200 may have various shapes within the scope of the embodiment.

The light emitting device package according to the embodiment can be used as a light source in various products, such as a lighting indicator, a character indicator, a lighting device and an image indicator.

In the description of the embodiments, it will be understood that, when a layer (or film), a region, a pattern, or a structure is referred to as being "on" or "under" another substrate, another layer (or film), another region, another pad, or another pattern, it can be "directly" or "indirectly" on the other substrate, layer (or film), region, pad, or pattern, or one or more intervening layers may also be present.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

INDUSTRIAL APPLICABILITY

The embodiments provide the light emitting diode capable of improving the light efficiency.

The embodiments provide the light emitting diode used as a light source in various products, such as a lighting indicator, a character indicator, a lighting device and an image indicator.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A light emitting device comprising:
a first semiconductor layer having nitride material;
a second semiconductor layer having nitride material;

an active layer between the first and second semiconductor layers;

an electrode layer on a central area of a surface of the second semiconductor layer;

a first electrode pad on the first semiconductor layer; and a second electrode pad on a peripheral area of the surface of the second semiconductor layer, wherein the first electrode pad includes a first adhesive layer, a first reflective layer, a second reflective layer, and a first barrier layer between the first reflective layer and the second reflective layer, wherein the second electrode pad includes a second adhesive layer, a third reflective layer, a fourth reflective layer, and a second barrier layer between the third reflective layer and the fourth reflective layer, wherein the electrode layer includes a light transmissive material, wherein the active layer emits light, and wherein a first portion of the light passes through the electrode layer and a second portion of the light is reflected by the second electrode pad.

2. The light emitting device of claim 1, wherein an edge portion of the second electrode pad is contacted with the electrode layer.

3. The light emitting device of claim 1, wherein first barrier layer and the second barrier layer comprises Ni or Ni—N.

4. The light emitting device of claim 1, wherein the first and second semiconductor layers are of different conductivity types.

5. The light emitting device of claim 1, wherein the first adhesive layer is in direct contact with the first semiconductor layer.

6. The light emitting device of claim 1, wherein at least a portion of the first semiconductor layer is greater in width than the second semiconductor layer.

7. The light emitting device of claim 6, wherein a first portion of the first semiconductor layer has a first width and a second portion of the first semiconductor layer has a second width, and wherein the first width is greater than a width of the second semiconductor layer and the second width is less than the first width.

8. The light emitting device of claim 1, wherein the first reflective layer is disposed between the first adhesive layer and the first barrier layer, and the second reflective layer is disposed on the first barrier layer.

9. The light emitting device of claim 1, wherein the electrode layer is a substantially transparent layer.

10. The light emitting device of claim 1, wherein the first electrode pad further includes a first light adjusting layer, wherein the second electrode pad further includes a second light adjusting layer, and wherein the second electrode pad is directly contacted with the electrode layer or the second conductive type semiconductor layer.

11. The light emitting device of claim 10, wherein the first and the second light adjusting layers are light reflective layers.

12. The light emitting device of claim 10, wherein the first light adjusting layer comprises a first reflective layer between the first adhesive layer and the first barrier layer, and a second reflective layer on the first barrier layer.

13. The light emitting device of claim 10, wherein the second electrode pad is directly contacted with the second conductive type semiconductor layer through an opening of the electrode layer.

14. The light emitting device of claim 11, wherein each of the reflective layers includes at least one selected from the group consisting of Al, Ag, an APC (Ag+Pd+Cu), an Al alloy and an Ag alloy.

15. The light emitting device of claim 11, wherein each of the light reflective layers has a thickness of about 1 to about 50,000 Å.

16. The light emitting device of claim 10, wherein the second light adjusting layer comprises a fourth reflective layer on the second barrier layer.

17. A light emitting device package comprising:

a package body;

the light emitting device of claim 1 electrically coupled to the package body;

a first lead coupled to the first electrode pad; and a second lead coupled to the second electrode pad.

18. The package of claim 17, wherein the first and second leads are formed over the package body.

19. The package of claim 17, wherein the light emitting device is coupled to a cavity in the package body.

20. The light emitting device of claim 1, wherein the first barrier layer and the second barrier layer comprises a single layer or a multiple layer.

21. The light emitting device of claim 1, wherein each of the first adhesive layer and the second adhesive layer has a thickness of about 1 to about 60,000 Å.

22. The light emitting device of claim 1, wherein the second electrode pad directly contacts with the second semiconductor layer.

* * * * *